United States Patent [19]
Griebel et al.

[11] Patent Number: 5,824,882
[45] Date of Patent: Oct. 20, 1998

[54] DEVICE FOR CHECKING THE POROSITY OF THIN RUBBER PRODUCTS

[76] Inventors: Robert Andre Emil Griebel; Gregory J. Gormley, both of 85 Justice Dr., Newtown, Pa. 18940

[21] Appl. No.: 776,826
[22] PCT Filed: Jul. 20, 1995
[86] PCT No.: PCT/DE95/00971
  § 371 Date: Mar. 26, 1997
  § 102(e) Date: Mar. 26, 1997
[87] PCT Pub. No.: WO96/03635
  PCT Pub. Date: Feb. 8, 1996

[30] Foreign Application Priority Data

Jul. 23, 1994 [DE] Germany ............. 44 26 225.6

[51] Int. Cl.⁶ .............. G01N 15/08; G01N 27/00; G01M 3/04
[52] U.S. Cl. ................... 73/38; 73/40; 324/557
[58] Field of Search ............... 73/38, 40; 324/557

[56] References Cited

U.S. PATENT DOCUMENTS

| | | | |
|---|---|---|---|
| 4,875,358 | 10/1989 | Marsh et al. | 73/40 |
| 5,196,799 | 3/1993 | Beard et al. | 324/557 |
| 5,389,097 | 2/1995 | Bennett et al. | 606/34 |
| 5,455,507 | 10/1995 | Horenstein | 324/557 |
| 5,499,898 | 3/1996 | Vonier et al. | 414/755 |
| 5,524,478 | 6/1996 | Joy et al. | 73/40 |
| 5,595,704 | 1/1997 | Hayashi et al. | 264/404 |

*Primary Examiner*—Hezron E. Williams
*Assistant Examiner*—Jay L. Politzer
*Attorney, Agent, or Firm*—Edwin D. Schindler

[57] ABSTRACT

Proposed is a device for testing the porosity of dielectric foil, particularly rubber products, such as condoms (2) with a cover holder over which the rubber product is placed, and of one or more outer electrodes (5), whereby the cover holder (1) and the outer electrodes (5) are connected to a source of voltage and an electrical gauge, whereby the outer electrodes (5) are in the form of points and the outer electrodes (5) and the cover holder (1) are relatively moveable toward one another so that the skin of the rubber product can gradually be scanned by the outer electrodes (5), and the gauge measures the flow of current in each electrode and by this measurement corresponds to the electrode in a reference measurement for the state in which there is an absence of material without the application of a rubber product, thereby showing a defect.

9 Claims, 3 Drawing Sheets

DEVICE FOR CHECKING THE POROSITY OF THIN RUBBER PRODUCTS

BACKGROUND OF THE INVENTION

1. Technical Field of the Invention

The invention concerns a device for checking the porosity of dielectric foils, particularly rubber products, such as condoms and protective gloves with a cover holder that is made of durable, electrically conductive material and over which the rubber product is placed, and of one or more outer electrodes that are on the side of the skin of the rubber product opposite the cover holder, whereby the cover holder and the outer electrodes are connected to a source of voltage and to an electrical gauge via electrical currents.

Other than for reasons of contraception, condoms are being increasingly regarded as protective devices against sexually transmitted diseases, particularly the virus that causes AIDS. Therefore, given the necessity of their impermeability for the essentially smaller viruses as compared to bacteria, the demand for condoms has inevitably risen. It is, however, a fact that latex, which is used to manufacture condoms, has shown in a number of cases such an evidence of pores that viruses are able to penetrate. The reason for this is that latex is constructed from interwoven macromolecules, thereby causing the manifestation of selective pores as well as a jagged surface with variable durability in the walls. The formation of porosity will never occur when other materials such as polyurethan are used. Nevertheless, the user is at a disadvantage here since polyurethan is plastic and therefore prevents the user from achieving the genuine feeling that he desires.

Given the fact that through the process of manufacturing condoms the impermeability of viruses cannot be guaranteed, testing each individual condom after manufacture is of great importance. Studies have shown that approximately 60% of condoms are virus-preventive. The remaining 40% percent, however, contains porous areas through which viruses can penetrate. Therefore, condoms do not offer 100% protection from infection. Doctors are well aware of this problem and consequently always use two pairs of gloves while operating in case they come into contact with blood. In this way, any areas on the gloves that may have pores can be physically separated from one another so as to essentially reduce the possibility of infection.

2. Description of the Prior Art

Existing procedures for testing the porosity of condoms consist in placing the condom on a metal cover holder and by means of an outer electrode measuring the condom's electrical resistance. Consequently, the condom is placed with a known device in a conductive fluid, whereby the outer electrode acts as the wall of the fluid bath. The disadvantages of this procedure are first that the condom must be dried immediately afterward and second that the entire surface must be integrally measured, which does not allow the individual pores to be localized.

In another procedure the outer electrode is a metal screen which is placed under high voltage, whereby the occurrence of disruptive discharges is measured. This procedure, however, is not foolproof given that the latex is selectively destroyed by the sparks emitted by the disruptive charges. Furthermore, the formation of ozone acts as a disadvantage.

Consequently, the purpose of the invention is to develop a device for testing the porosity of condoms in such a way that individual pores can be determined and localized within a diameter of 25 to 75 nanometers.

SUMMARY OF THE INVENTION

The invention will carry out its task based on the following data: the outer electrodes are in the form of points; the outer electrodes and the cover holder are relatively moveable toward one another so that the skin of the rubber product is gradually scanned by the outer electrodes; the current produced from the source of voltage between the cover holder and the outer electrodes is an alternating current or pulsating direct current; the gauge measures the flow of current in each electrode and by this measurement corresponds to the electrode in a reference measurement for the state in which there is an absence of material without the application of a rubber product, thereby showing a defect.

The fundamental reasoning behind the invention is that point electrodes, not an extensive outer electrode, will be used to carry out the task. Since each individual electrode is utilized according to measurement technology, it is possible to detect, show and localize individual pores. In order to test the entire surface of a condom, the entire surface is scanned by the outer electrodes, meaning that each point of the surface of the condom must have at least once during the process of measurement fallen short of a definite maximal distance dependent on the measurement parameters to one of the electrodes. An alternating voltage lies between the outer electrodes and the cover holder: given the capacity between the outer electrodes and the cover holder this results in an alternating current which is measured separately for each outer electrode. Since latex has a dielectric number relatively different from air, areas where no latex is present show another capacity than areas with a latex coating. The measurement procedure is so sensitive that pores having a size of 10 muon meters result in such a change in capacity that this change is ascertained by the measuring device through the recording of the flow of current. If the evaluation of the individual currents of the outer electrodes reveals a defect, then this will be indicated on the measuring device. In fact, results are obtained during the gradual process of measurement based upon the existence of pores of greater or smaller diameters in comparison, to the individual measuring points in for instance continuous transitions. By official verification the corresponding diameters of the pores can be assigned. By indicating a threshold value all the pores above the minimal diameter indicated by the threshold value can be recorded and shown. By means of scanning the entire surface is recorded; by maintaining a constant distance of electrodes the measurements can immediately be compared with one another. Otherwise, a conversion to standardization must result.

The overall advantages of the invention are that individual pores can be detected and that the measurement is foolproof.

Given the high voltage involved it is recommended for reasons of safety that either a cover holder or the outer electrodes be used.

Scanning the condom can be particularly effective if the cover holder is turned around its rotation axis, the result being that the outer electrodes do not revolve tediously around the cover holder but remain steadfast.

The measurement procedure is made even easier if the outer electrodes are concentrated in an electrode holder so that they can be moved simultaneously by a drive.

One preference regarding the arrangement of the outer electrodes on the electrode support is that the outer electrodes be arranged side by side along a straight line, whereby neighboring outer electrodes show a constant distance. The advantage here is that large areas can be scanned very quickly.

Another aspect of the invention involves setting several rows alongside one another so that the respective gaps of the rows of electrodes are recorded. By moving this kind of electrode holder perpendicularly, whereby the rows can run their course relative to the condom, the coated areas can be measured on the surface.

As an advantage the rows run parallel to the rotation axis of the cover holder. The reason here is that because of the turning of the cover holder it is not effective for the outer electrodes to run ring-like around the condom. Because of the turning itself all the points located on the ring affected by the outer electrode can be reached.

As a rule it is sufficient to set two rows of outer electrodes halfway at the electrode distance in order to facillitate a measurement on the surface.

In addition, by rotating the cover holder it is possible to move the electrode holder parallel to the rotation axis of the rover holder up and down so that the number of points coated by the outer electrodes can be increased.

Moving the lift of the electrode holder by means of curve gears can prove itself an advantage.

In order to lessen the build up of ozone, which inevitably forms with the application of high voltage, a protective gas, particularly nitrogen, is conducted between the outer electrodes and the surface of the condom. This is another aspect of the invention. This supplying of protective gas can be integrated into the electrode holder.

Technically speaking, the destructive effect of the sparks emitted by the disruptive charges has already been explained. In order to suppress this, it is recommended that an electrical isolator pointed toward the rubber product and the cover holder be fastened. One of the preferred materials here is aluminum oxide (Alo).

BRIEF DESCRIPTION OF THE DRAWING FIGURES

Further details, characteristics and advantages of the invention can be found in the following section, where a more accurate explanation of a suggested way to use the invention is provided by means of schematic illustration. These are FIG. 1 Device for testing condoms with a rotating cover holder in cross-section along the rotation axis of the cover holder FIG. 2 Partial cross-section through an electrode holder FIG. 3 Greatly enlarged part of a condom situated on the cover holder

DETAILED DESCRIPTION OF THE DRAWING AND PREFERRED EMBODIMENTS

Figure 1:
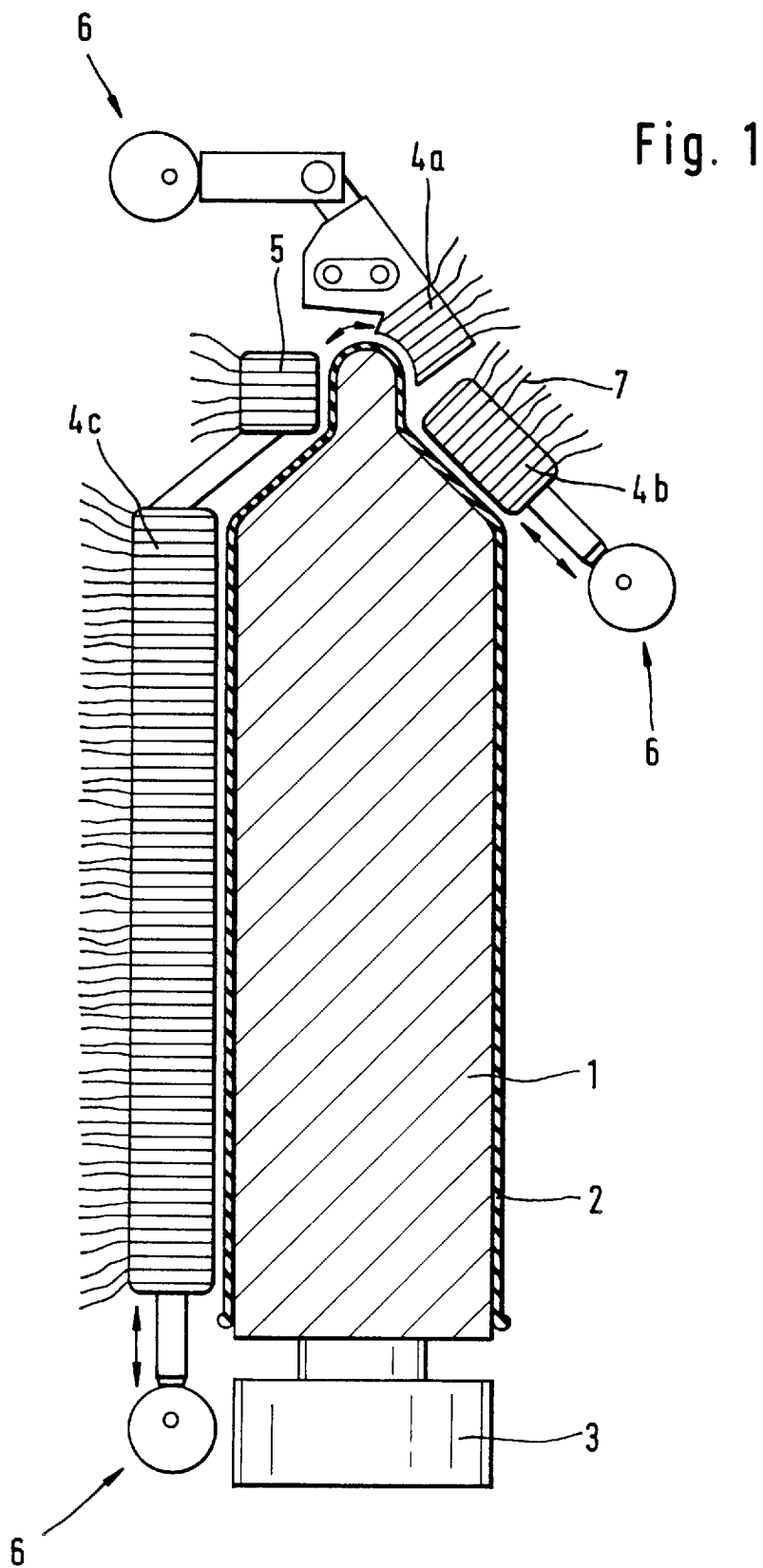

Shown in FIG. 1 is a cover holder (1) that is rotation symmetrical, essentially cylindrical and ending in a rounded head. A condom (2) is unrolled on the cover holder. At the opposite end of the rounded head of the cover holder (1) we see the cover holder connected to a rotation drive (3). Directly on the rounded head of the cover holder (1) there is a corresponding small, rounded electrode holder (4a) in a row of outer electrodes (5) on the side of the condom opposite the cover holder (1). The section of the head is covered to the straight, cylindrical part of the cover holder (1) by a middle electrode holder (4b), whose outer electrodes (5) are lined up along a straight side of the head to the beginning of the straight part of the cover holder. Finally, the straight, cylindrical part of the cover holder (1) is scanned by a large electrode holder (4c), whose outer electrodes (5) are on a straight line parallel to the rotation axis of the cover holder (1). All the electrode holders (4a, 4b, 4c) are connected to curve gears (6), moving up and down along the rows of outer electrodes (5). Each outer electrode (5) is connected to a measuring device via an electrical current (7). (This is not depicted).

Figure 2:
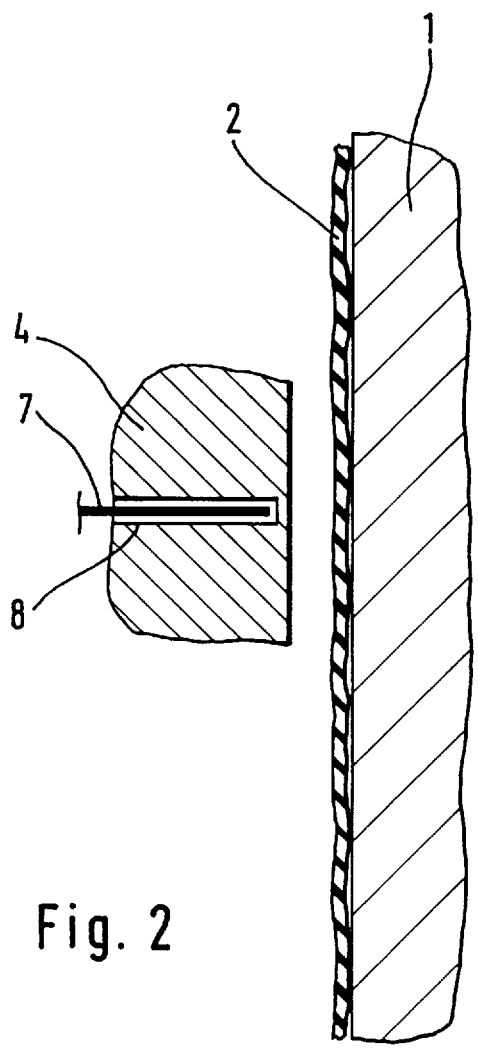

FIG. 2 shows a part of one of the three electrode holders (4a, 4b, 4c). The outer electrode (5) itself is a plate that is on the surface of the electrode holder (4a, 4b, 4c). The plate is connected to an electrical current (7), which is led through a bore-hole (8) through the electrode holder (4a, 4b, 4c) to the opposite side and then to the measuring device (not depicted). At a distance from the outer electrode (5) the condom is rolled (2) over the cover holder (1).

Figure 3:
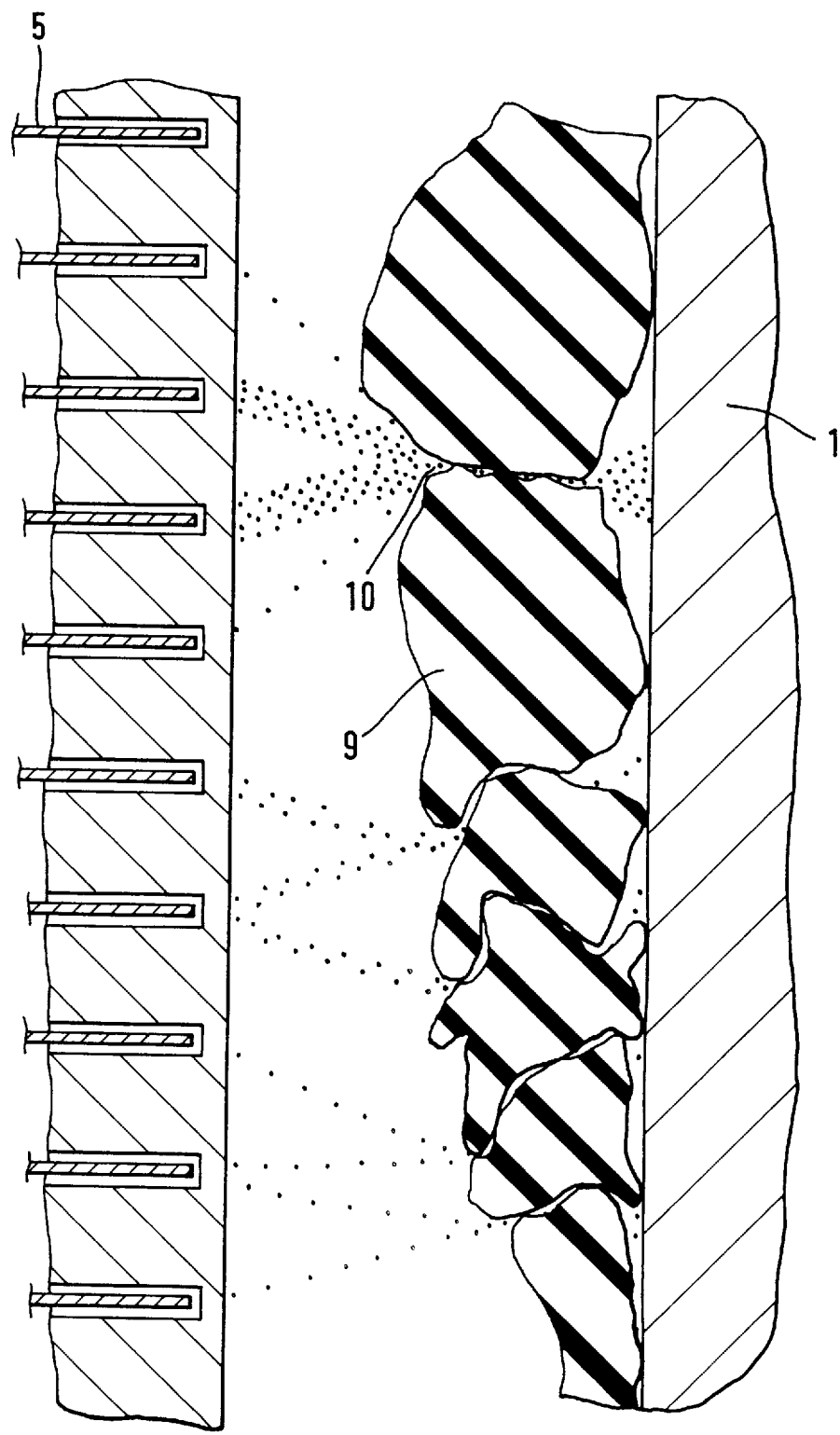

In FIG. 3 an unrolled condom (2) over the cover holder (1) is greatly enlarged. The condom (2) is also interwoven and constructed from split macromolecules, showing a relatively large pore (10) in one place. Outer electrodes (5) are arranged over the condom at an equal distance. The electric field, which is relatively inhomogenous because of the pore (10) and stands between the outer electrodes (5) and the cover holder (1), is indicated by field lines.

What is claimed is:

1. Device for checking the porosity of dielectric foils, particularly rubber products, such as condoms or protective gloves, which have a cover holder made of durable, electrically conductive material and over which the rubber product is placed, and a plurality of outer electrodes that are on the side of the skin of the rubber product opposite the cover holder, whereby the cover holder and the outer electrodes are connected to a source of voltage and an electrical gauge via electrical currents, wherein:

the outer electrodes are in the form of points, the outer electrodes and the cover holder are relatively moveable toward one another so that the skin of the rubber product is gradually scanned by the outer electrodes, the voltage produced from the source of voltage between the cover holder and the outer electrodes is an alternating current or pulsating direct current, the gauge measures the flow of current in each electrode and by this measurement corresponds to the electrode in a reference measurement for the state in which there is an absence of material without the application of a rubber product, thereby showing a defect.

2. Device in accordance with claim 1, wherein either the cover holder or the outer electrodes are electrically on ground potential.

3. Device in accordance with claim 1, comprising a rotation drive wherein the cover holder is rotation symmetrical and that the rotation drive turns the cover holder around its rotation axis.

4. Device in accordance with claim 1, wherein several outer electrodes are concentrated in an electrode holder.

5. Device in accordance with claim 4, wherein the outer electrodes are arranged in straight rows.

6. Device in accordance with claim 5, wherein the electrode holder shows at least two parallel rows of outer electrodes, whereby the distance between electrodes along the rows is identical and the rows are set relative to one another at a quantity in a longitudinal direction, the quantity being smaller than the distance between electrodes.

7. Device in accordance with claim 1 comprising a protective gas supply which conducts protective gas, particularly nitrogen, between the outer electrodes and the skin of the rubber product.

8. Device in accordance with claim 7, wherein the protective gas supply is integrated in the electrode holder.

9. Device in accordance with claim 1, wherein the outer electrodes directed to the rubber product are provided with an electrically isolating layer, which is not present at an electrode tip.

* * * * *